(12) United States Patent
Braun et al.

(10) Patent No.: US 6,376,251 B1
(45) Date of Patent: Apr. 23, 2002

(54) ON-SITE DRUG TESTING METHOD

(75) Inventors: Richard J. Braun, Plymouth; James A. Schoonover, White Bear Lake, both of MN (US)

(73) Assignee: MedTox Scientific, Inc., St. Paul, MN (US)

( * ) Notice: Subject to any disclaimer, the term of this patent is extended or adjusted under 35 U.S.C. 154(b) by 0 days.

(21) Appl. No.: 09/358,340

(22) Filed: Jul. 21, 1999

Related U.S. Application Data (60) Provisional application No. 60/118,452, filed on Feb. 3, 1999.

(51) Int. Cl.[7] .............................................. G01N 35/00
(52) U.S. Cl. ...................... 436/43; 235/462.13; 702/84; 700/266
(58) Field of Search ...................... 436/43; 235/462.13; 702/84; 700/266

(56) References Cited

U.S. PATENT DOCUMENTS

| 5,902,982 A | | 5/1999 | Lappe | 235/375 |
|---|---|---|---|---|
| 5,916,815 A | * | 6/1999 | Lappe | 436/92 |
| 5,929,422 A | | 7/1999 | Lappe | 235/462.13 |
| 6,036,092 A | * | 3/2000 | Lappe | 235/462.13 |
| 6,055,487 A | * | 4/2000 | Margery et al. | 702/84 |
| 6,171,112 B1 | * | 1/2001 | Clark et al. | 434/322 |

* cited by examiner

Primary Examiner—Nina Bhat
(74) Attorney, Agent, or Firm—Schwegman, Lundberg, Woessner & Kluth, P.A.

(57) ABSTRACT

The invention described herein includes a method of testing an analyte such as urine to determine whether the analyte contains specific substances such as drugs of abuse. An on-site screening test provides a preliminary test result either by visual or machine analysis of a screening test device, and the result and user data are entered on a provided form. An electronic image of the form is sent to a central data location, where it is received and the data on the form is recognized by machine and stored. If the on-site screening test provided a nonnegative result a sample is sent to a laboratory for further testing, and if the test provides only negative results no further testing is done. The testing laboratory performs further testing for verification of nonnegative screening test results, and all data is collected at the central data location. Results are then reported to the client or whoever the client designates to receive test results.

21 Claims, 7 Drawing Sheets

ON-SITE DRUG TESTING METHOD

CLAIM OF PRIORITY

This application is based on provisional application No. 60/118,452 filed Feb. 3, 1999, and claims priority therefrom.

FIELD OF THE INVENTION

The invention relates generally to testing an analyte for presence of a selected substance, and more specifically to a method for testing urine or other bodily fluids for selected drugs.

BACKGROUND OF THE INVENTION

Employers today often require prospective employees to undergo preemployment drug screening, to test for use of selected illegal drugs. Testing for drugs is done not only to ensure that an employer is hiring employees whose work will not be affected by drug use, but also to screen for drug use in other environments. For example, those undergoing drug use rehabilitation may undergo regular drug tests to ensure that they are no longer using drugs. Prison residents may also be subjected to regular drug tests to ensure that they are not using drugs in prison. Selected employees in jobs with a high degree of responsibility may be regularly screened for drugs, such as truck drivers being screened to ensure they are not using drugs while driving and law enforcement officers being screened for drugs to ensure their actions while working are not affected by drug use.

Typically, a prospective employee or other test subject is asked to provide a urine sample in a controlled environment, and the sample is sent to a laboratory to be tested for drug presence. This requires that the urine sample be positively identified and securely shipped to the laboratory, where the sample and the results of the test must be matched to the person undergoing the drug screening. The employer must then not only wait for the transported sample to arrive at the lab, be tested, and for results to be sent back, but must undergo the expense of transportation and laboratory testing for each subject tested for drugs.

On-site tests exist to provide initial screening results, and so can provide an initial indicator of whether the subject has used drugs recently, but are not sufficiently accurate to replace laboratory testing as a legally defensible means of confirming the presence of illegal drugs. The on-site screening tests may however be made sensitive enough to reliably indicate that a subject may have used drugs when predetermined quantities of illegal drugs are present in the subject's urine. A non-negative indication from an on-site screening device is therefore not a positive indication of drug use, but an indicator that the subject very likely may have used drugs. However, a negative indication from an on-site screening device indicates that the test subject is extremely unlikely to have sufficient quantities of illegal drugs in his urine to fail a laboratory screening test. This means that a negative result can be reliably used to determine that a subject has not used drugs and no further testing is necessary, but a non-negative result requires verification by a laboratory before concluding the subject has used drugs.

But, the problems of communicating results between the on-site screening site, the testing laboratory, and the client remain, as do the problems with tracking shipped urine specimens for non-negative on-site test results. What is needed is an inexpensive and efficient means to collect and communicate this information, and to track data related to each test subject.

SUMMARY OF THE INVENTION

A method for testing an analyte for the presence of selected materials is provided, including a method of efficiently and inexpensively managing related data. In one embodiment, a trained and certified collector collects a urine sample in one or more containers that may be sealed, and the seals are verified by the test subject. An on-site screening test is performed and a provided form is completed with screening test results, test subject identification, and chain-of-custody information. An electronic image of the form or other representative data is then sent to a central data location where it is automatically recognized and the data written thereon is stored. In one embodiment, an on-site screening test device reader reads data from the test device and sends the information to the central data location. A container and a paper copy of the form or other identifying data are sent to a lab if the screening test result is nonnegative. The lab receives the container and tests the urine, recording the results with the data recognized and stored from the form image. The combined stored data is then sent to the client requesting the test.

DETAILED DESCRIPTION

In the following detailed description of sample embodiments of the invention, reference is made to the accompanying drawings which form a part hereof, and in which is shown by way of illustration specific sample embodiments in which the invention may be practiced. These embodiments are described in sufficient detail to enable those skilled in the art to practice the invention, and it is to be understood that other embodiments may be utilized and that logical, mechanical, electrical, and other changes may be made without departing from the spirit or scope of the present invention. The following detailed description is, therefore, not to be taken in a limiting sense, and the scope of the invention is defined only by the appended claims.

The invention relates to testing a collected analyte such as a urine sample for selected substances such as drugs of abuse, and a method for inexpensively electronically communicating, managing, and reporting the related data. The method comprises in part entering data such as identification data, on-site test screening results, and chain-of-custody information on a provided form or other data collection means, and sending an electronic image of the form or other representation of the collected data to a central data location where it is recognized and the data is stored.

The electronic image may be sent by means of a normal fax machine or other electronic communication device, thereby requiring only standard inexpensive office equipment in some embodiments at each of the several remote testing sites. Also, an on-site test device reader may read the on-site test device data and display the data to be recorded on the provided form or may electronically send the data to a central data location.

Figure 1:
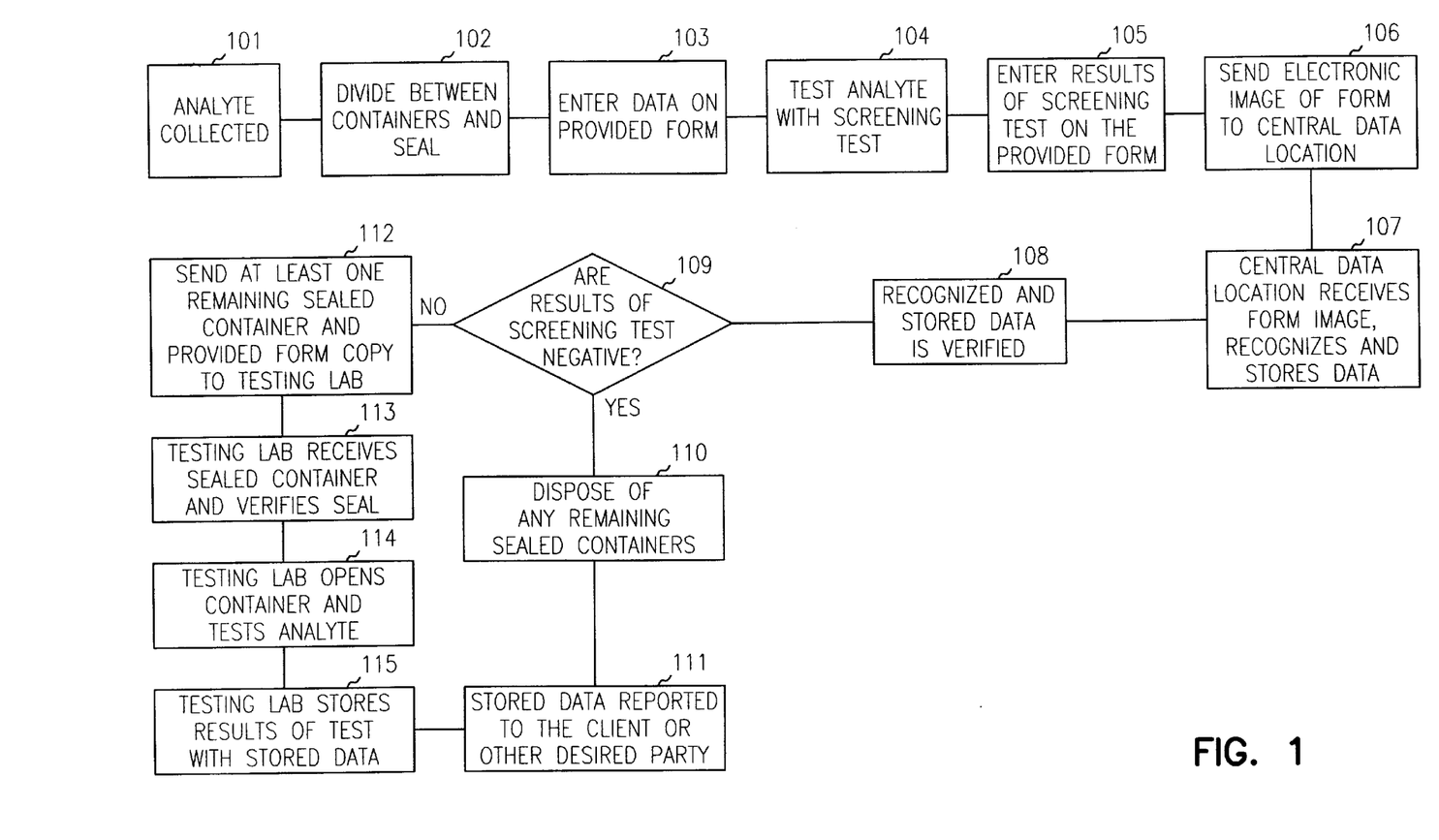
FIG. 1 shows a flowchart of a method of testing a urine sample, consistent with an embodiment of the present invention.

FIG. 1 shows a flowchart detailing the method of collecting and testing a urine sample analyte and electronically managing the related data. Although the blocks of the flowchart are discussed and numbered in a certain order, they need not necessarily be performed in that order. At 101, a urine sample is collected from the test subject. The urine sample is immediately placed in one or more specimen cups such that at least 30 ml of urine is in each cup in 102, and one or more of the cups are sealed. The seal of one embodiment comprises both a unique barcode that matches a barcode on the provided form and initials or a signature verifying the specimen cups were sealed in the presence of the test subject. A thermometer strip attached to the specimen cup in a further embodiment indicates the temperature of the urine to ensure that the urine is near body temperature and so provided from the test subject rather than from a container.

At 103, data is entered on a provided form. The data on the form includes information to identify the test subject, information about the person collecting the specimen and performing the on-site screening test, the temperature of the urine sample, and chain-of-custody information. One specimen container is opened at the remote collection site, and urine contained therein is used for an on-site screening test at 104. The screening test of one embodiment is performed with the device pictured in FIG. 3 and later described. The results of the screening test are then entered with the other data on the provided form at 105, and an image of the form is sent electronically to a central data location at 106. Sending the image of the form in one embodiment is done by fax or other electronic communication device, requiring only an electronic communication device such as a standard inexpensive fax machine to electronically communicate data with the central data location.

Figure 3:
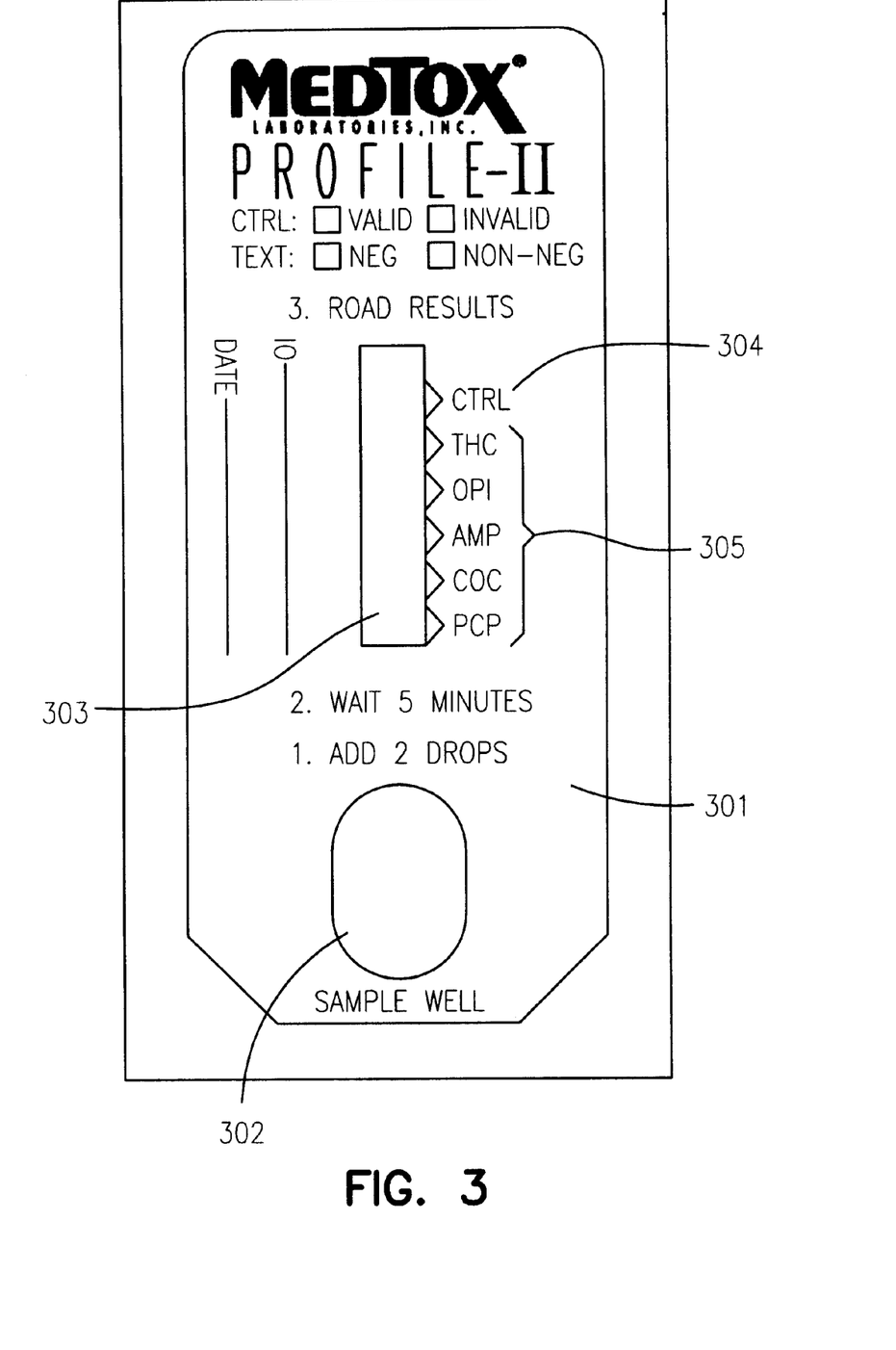
FIG. 3 shows an on-site screening device consistent with an embodiment of the present invention.
Figure 5:
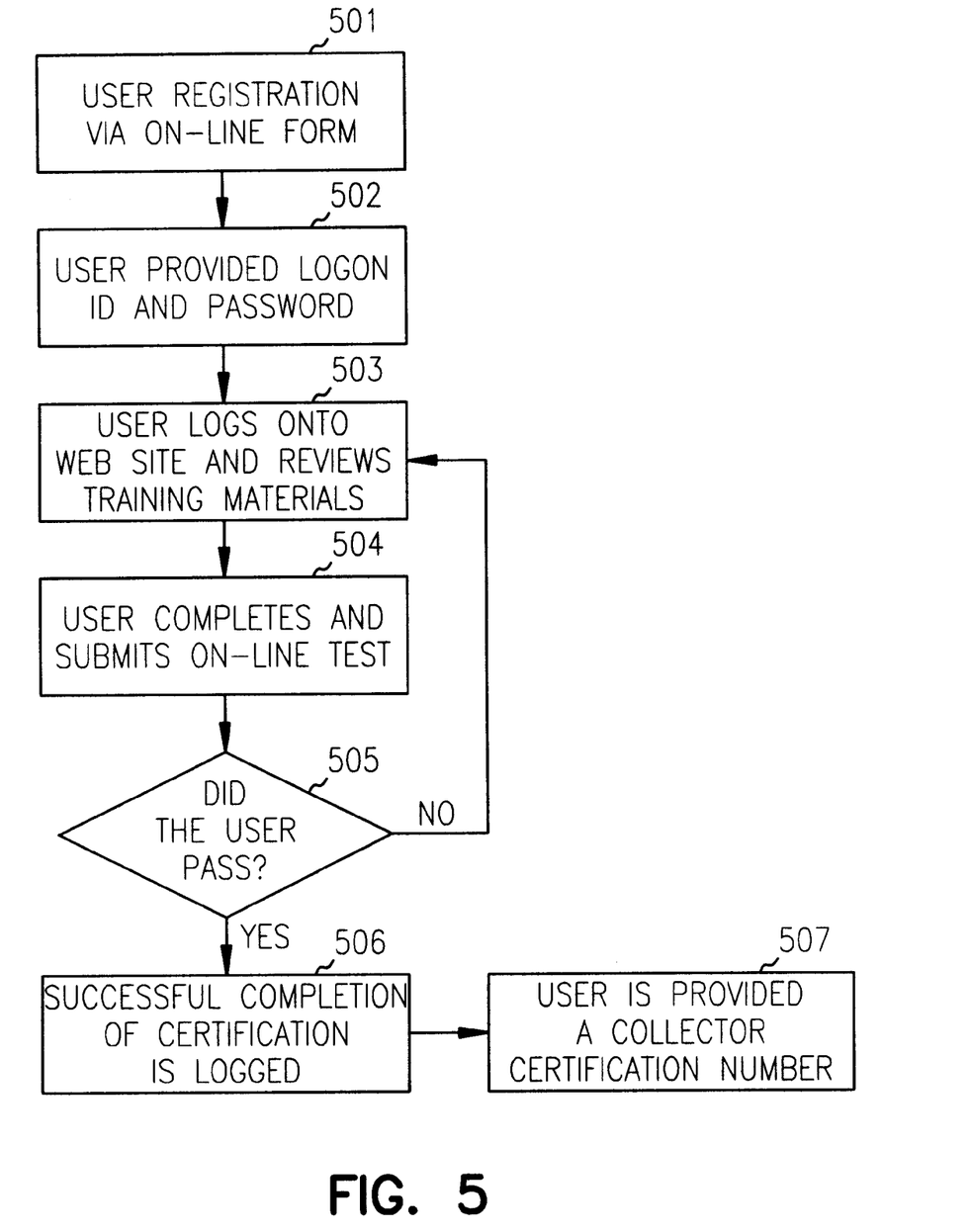
FIG. 5 shows a flowchart of on-line training and certification, consistent with an embodiment of the present invention.

In another embodiment, the screening test at 104 is done with the screening test device pictured in FIG. 3 which is then read by an on-site screening device reader pictured in FIG. 5. The results of the screening test as indicated by the screening device reader may be entered on the printed form with other data at 105, or may be electronically sent to the central data location as later explained. The screening test of a further embodiment also includes screening an analyte sample for presence of adulterants and reporting the results of the adulterant screening along with the results of the screening test.

The central data location automatically receives the electronic image of the form at 107, and recognizes the form and the data entered thereon and stores the data. In embodiments where a screening device reader is implemented, the central data location also receives the screening device data sent by the reader. Recognizing the data from the form includes reading the barcode preprinted on the form, as well as recognizing the text and checked boxes that indicate other data. Recognition of the barcode enables coordination of data received from multiple sources, so that all data associated with a particular barcode number can be stored and referenced together. The stored data is then verified for accuracy at 108, with special attention given to accurate recognition of the results of the on-site screening test. If a recognition error occurs such that the image data is inconclusive, the erroneous data is flagged and a call is made to the on-site remote screening location to verify the information.

If the results of the on-site screening test are negative at block 109, other containers with a portion of the urine sample are disposed of at 110, and the stored data is reported to the client at 111. If the results of the on-site test are non-negative at block 109, at least one remaining sealed container and a paper copy of the provided form are sent to the testing lab at block 112. The testing lab receives the sealed container and verifies the seal at block 113. The lab then opens the container and performs a laboratory test for selected drugs of abuse at 114, where the laboratory tests consist of one or more of an immunoassay, gas chromatography, or mass spectroscopy. The laboratory tests also screen for adulterants that may be used to attempt to disguise the presence of selected drugs in the subject's urine. The testing lab then stores the results of the laboratory tests with the stored data at 115, and the combined stored data is reported to the client at 111. The client may include one or more of the on-site remote screening site, a client's office, a corporate medical information officer, or any other party to whom the client desires test results be sent.

The results may be sent via fax, electronic mail, mail or courier service, or any other means of safely and securely sending the report to the client. Interactive reporting of results may also be provided, such as by an interactive voice response system, interactive computer-based reporting system, interactive telephone touch-tone system, or other similar system. The report given to the client may take many forms, including a summary of tests performed over a particular period of time or detailed information regarding a particular test subject. The stored information may also be used to populate a financial database for billing the client, or for populating a laboratory database or a statistical database.

Figure 2:
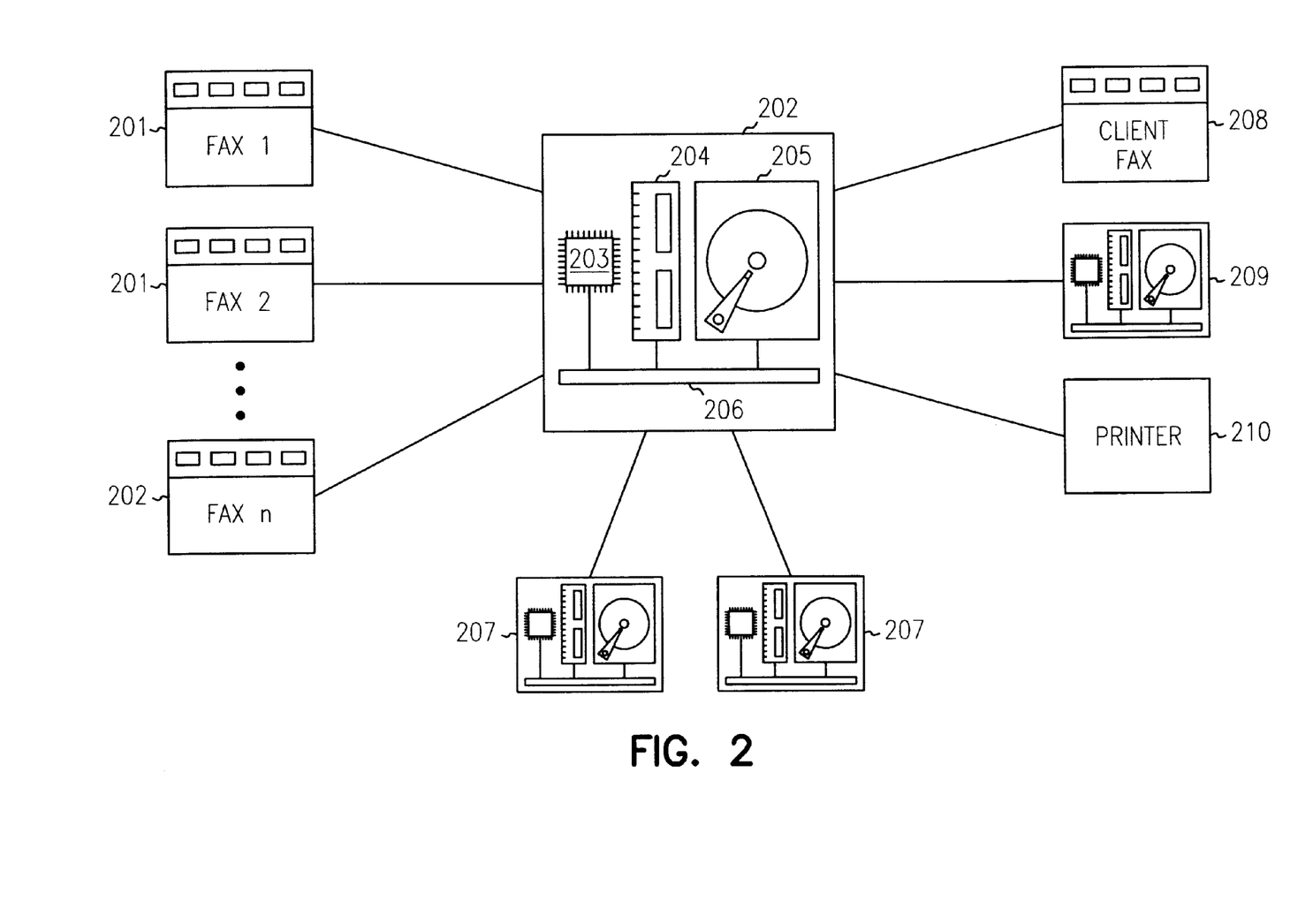
FIG. 2 shows data communication apparatus consistent with an embodiment of the present invention.

FIG. 2 shows a hardware communications system operable to practice one embodiment of the present invention. A fax machine 201 is located at each of one or more on-site remote screening sites, and is connected via a normal telephone dialup connection to a computer 202 at a central data location. The computer contains a processor 203, a memory 204, and hard disk storage 205, connected by a bus 206. The central data system 202 is also connected to one or more laboratory computers 207. Finally, the central data system reports data to the client through one or more of a client fax 208 accessed via a normal dial-up telephone connection, a client computer system 209 accessed via a dial-up connection or Internet connection, or a printer 210 used to print test results that are mailed to the client.

The fax machine 201 scans the provided form with data entered and creates an image of the form that is transmitted to the central data system computer 202. The central data system computer has software executing thereon that causes the computer to automatically receive the incoming electronic image and recognize the data thereon. The recognized data is stored in the system on hard drive 205, along with data entered by the testing laboratory that is associated with recognized data from test subjects with nonnegative on-site test results. The combined data is then sent to the client via an electronic communication such as through a client fax machine 208, a connected client computer 209, or a connected printer 210. In an alternate embodiment, an interactive response system is employed, such as a telephone voice interactive response system.

FIG. 3 shows the on-site test device used in one embodiment of the present invention. The device is the Profile II (TM) device 301, made by Medtox Diagnostics, Inc. (TM). The device is a qualitative single-step analytical test, designed to detect the presence of selected substances in an analyte. In a further embodiment, the Profile II device is designed specifically to detect the presence of selected drugs of abuse in urine at levels that meet or exceed the specific cut-off levels recommended by the Substance Abuse and Mental Health Administration.

An analyte, such as urine from a test subject, is placed in the sample well 302 to begin the test. In one such embodiment, the urine analyte wicks up the indicator strip 303, where it reacts with the detection system and after a short reaction time provides a visual indication of the presence of selected drugs of abuse in the urine. For the test to be valid, a line must have formed on the test strip adjacent to the CTRL control indicator 304. If a drug being tested for is not present in the urine, a line is observed next to the indicator for the drug shown at 305. If a line fails to form on the test strip 303 adjacent to any of the indicators 305, the test is non-negative for the presence of that particular drug in the tested urine.

The device of this embodiment uses a gold colloid detection system, with monoclonal antibodies in a competitive inhibition format to detect the presence of drugs in the urine sample. Mouse monoclonal antibodies that are specific to each of the five drugs screened for by the Profile II device shown at 301 are bound to gold colloid particles. The two drops of urine mobilize the gold colloid, and the monoclonal antibodies for a specific drug will bind to them if the specific drug is present in the urine sample. The drugs bind to the limited number of binding sites on the antibody/gold complex, and so will not be available to bind to the drug conjugate on the indicator strip.

Figure 4:
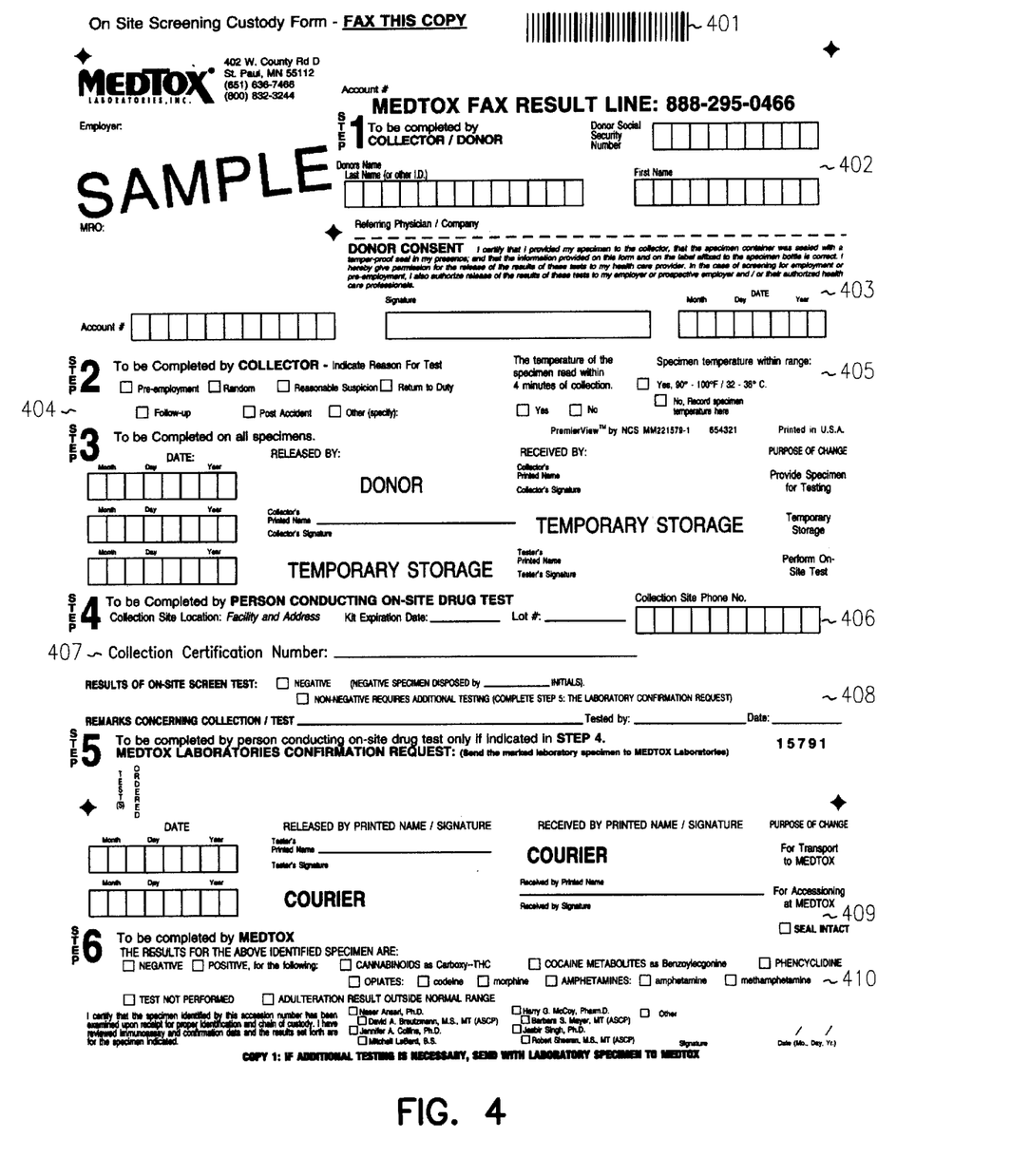
FIG. 4 shows a provided form consistent with an embodiment of the present invention.

FIG. 4 shows a form that may be used in one embodiment of the invention. The provided form has a barcode located thereon, shown at 401. Identification information for the test subject is entered at 402, including name or social security number, or some other positive identification number to identify the test subject. The test subject completes the donor consent portion at 403, verifying the specimen was properly given and sealed, and granting permission for the testing company to release the results of the test to the client. The person conducting the on-site test indicates the reason for the test by checking a box or filling in a text box at 404, and indicates the temperature of the urine sample as indicated by the thermometer strip on the sample container at 405. The person conducting the on-site test enters information regarding the identity and contact information for the collection site at 406, and enters a collector certification number issued to the collector to verify proper training and certification at 407. The result of the on-site screening test is indicated at 408, and the tester signs the chain-of-custody information record at 409.

The sample is released to the custody of a courier who takes possession of the packaged sample and delivers it to the testing laboratory. The person receiving the sample at the testing laboratory also signs the chain-of-custody information field at 409. The testing laboratory tests the urine sample, and indicates who performed the test and the results of the test by checking the appropriate boxes in the test results area 410.

The provided form shown in FIG. 4 in different embodiments of the invention may be provided as a preprinted form, may be provided electronically to be printed, may be provided and completed electronically, or may be a similar means for collection of such data.

The person collecting the urine sample or other analyte is certified as properly trained in one embodiment by reviewing training materials and taking a certification test. The certification test may be administered by traditional means such as completion of a paper test or by electronic means such as via an Internet web site. In a further embodiment, the web site or other electronic means provides other functionality such providing training information, allowing ordering of supplies such as analyte containers and forms, and registration for testing. In one embodiment, the tester is certified by reviewing materials provided via an Internet web site, and by successfully completing an on-line test. A collector certification number is provided to identify testers who have completed the on-line training and certification process, and is used to verify proper training of those who collect samples or order on-site testing materials.

FIG. 5 shows a flowchart illustrating the online training and certification process of one embodiment. At 501, a user registers by completing an on-line form including identity and contact information, such as a telephone number or e-mail address. At 502, the user is notified via the provided contact information that his registration has been accepted, and is provided a logon ID and password. At 503, the user logs on to the web site providing on-line training materials, and reviews the training material. After completing the training materials, the user takes an on-line test at 504. At 505, the on-line test is evaluated to determine whether the user has achieved a passing score. If the user does not pass, the user can again review the training materials at 503 and retake the on-line test. If the user passes the test, successful completion of the test is logged at 506. In a further embodiment the user is also provided a collector certification number at 507, such as is entered at the collector certification number field at 407 of the provided form in FIG. 4.

Figure 6:
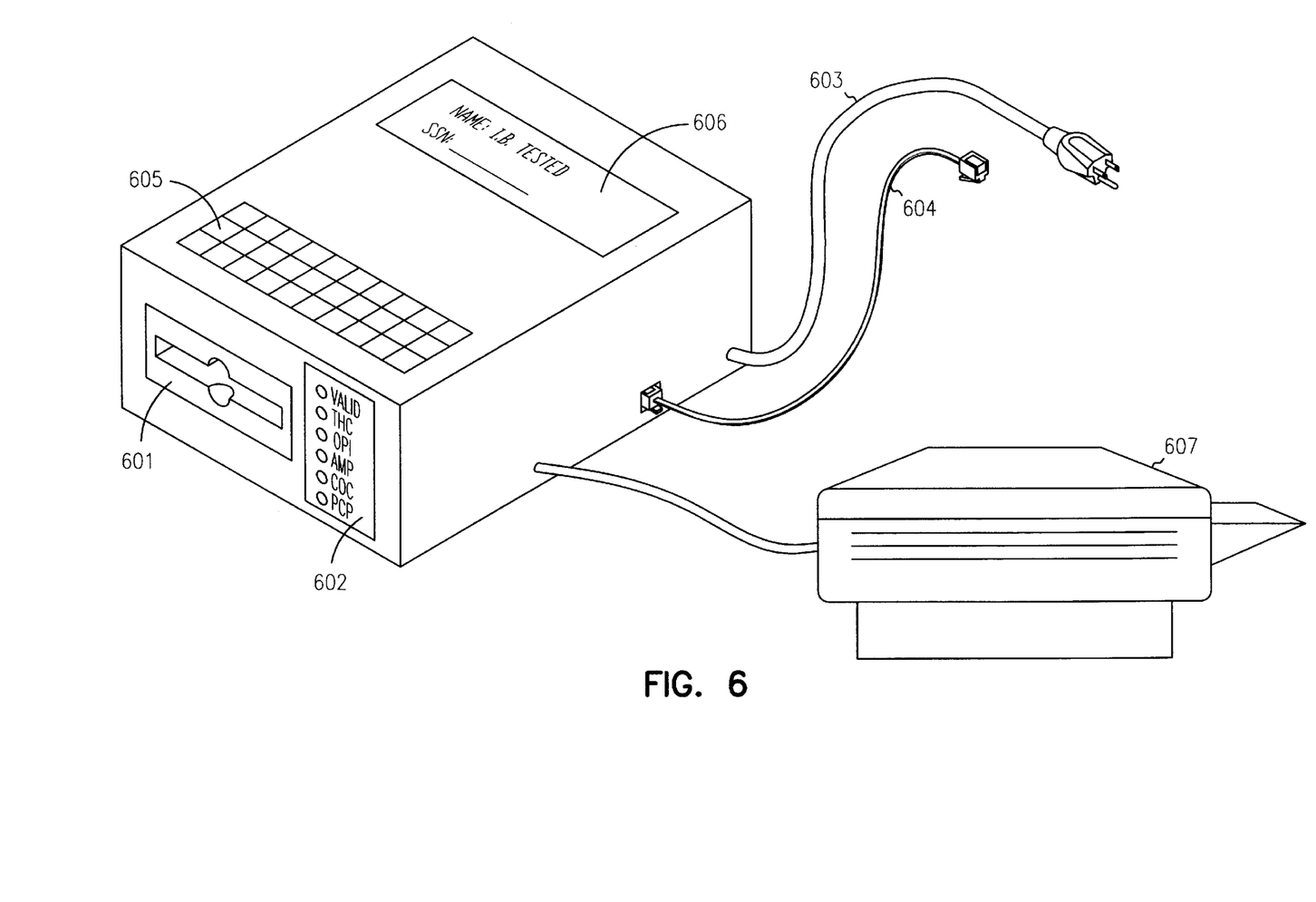
FIG. 6 shows an on-site screening device reader consistent with an embodiment of the present invention.

FIG. 6 shows one embodiment of an on-site test device reader that is operable to read data from an on-site test device such as is pictured in FIG. 3. The reader has an optical scanner 601 designed to receive and optically scan an on-site test device. The reader of one embodiment further has a plurality of indicator lights 602 that are labeled to indicate meaning. A power cord 603 plugs in to a standard wall outlet to provide power, and a telephone cord 604 is attached to provide a connection to a telephone network. The reader may also contain a keyboard 605 and an alphanumeric display 606 to enter and view data. A printer 607 may also be attached or incorporated into the reader.

To operate the on-site test device reader, the test device of FIG. 3 is inserted into the optical scanner 601, and an optical scan of the test device is performed. The reader of one embodiment stores a scanned image of the test device, while in an alternate embodiment the reader analyzes the optical scan of the test device to automatically determine the result of the onsite test. The reader analyzes the optical scan by recognizing the presence or intensity of lines produced as a result of the on-site test, during which lines are formed on the test device as explained previously in the description of FIG. 3. If the reader is capable of analyzing the optical scan, results are displayed via indicator lights 602 or an alphanumeric display 606. Displaying results via indicator lights 602 includes in one embodiment illuminating lights associated with labels to indicate that a test is valid, and to indicate a nonnegative test result for specific selected substances being tested for. Displaying results via alphanumeric display 606 comprises displaying text indicating a scan of the test device indicates the test was valid, as well as displaying text indicating nonnegative test results for the presence of selected substances. A keyboard 605 may be used to instruct the reader to display various results, to enter data related to the current test device being read, or to control operation of the reader.

For example, a test device may be optically scanned and data such as a barcode number identifying the test subject may be entered into the reader via the keyboard 505 or via some other means such as a barcode reader. Other information such as name and social security number may also be entered via keyboard 605, and is associated with the optically scanned test device information. The identifying information may then be printed along with test results to a printer 607, or sent to the central data location via a connection 604 to a telephone network. In other embodiments, other means of electronic communication may be used, such as via the Internet.

In an embodiment where test information such as name, social security number, specimen temperature, or other test-related information are entered into the reader and sent to the central data location via telephone network, such data need not also be entered on the form shown in FIG. 4. The data need not be repeated because the data provided from the reader is combined at the central data location with data from the provided form and from the laboratory by matching the barcode number or other identifying information associated with the stored data. Data such as the results of the test may however be entered both on the form and reported by the reader via electronic network to the central data location where the data is compared to verify that data reported for the same test subject from multiple sources is consistent, thereby ensuring reporting accuracy.

Figure 7:
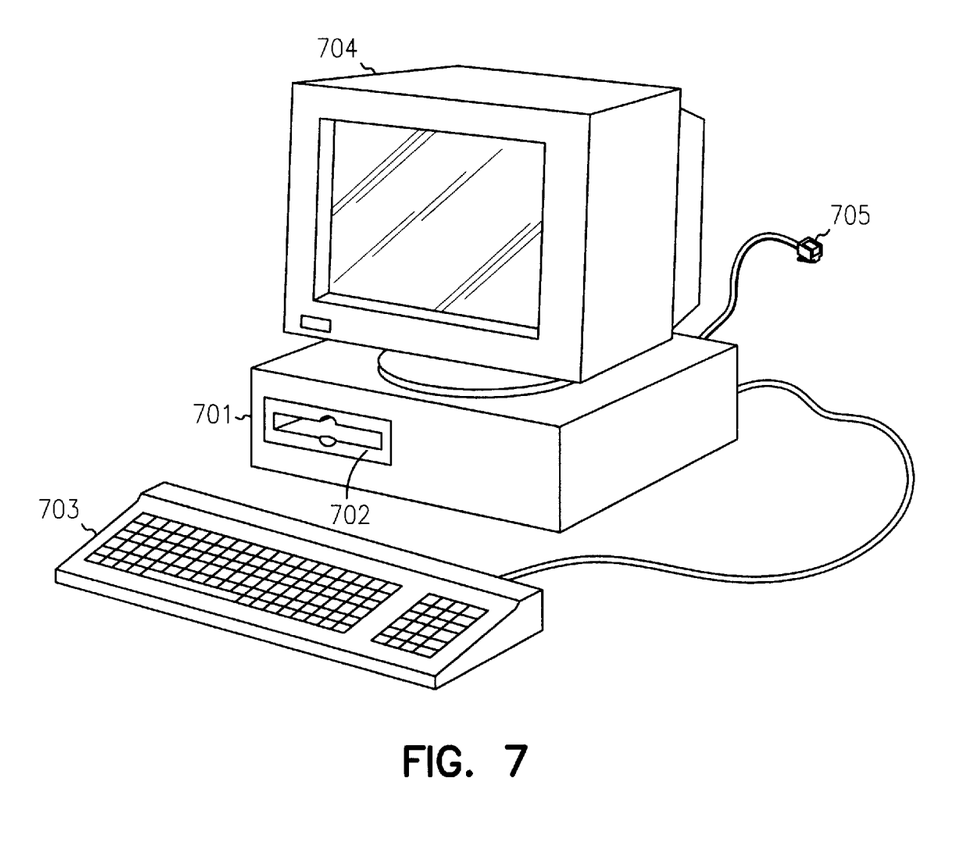
FIG. 7 shows a computer with an optical scanner, consistent with an embodiment of the present invention.

In another embodiment, the optical scanner is incorporated into a general purpose computer system, as shown in FIG. 7. A computer 701 has within it an optical scanner 702 designed to receive and optically scan an on-site test device. The computer has a keyboard 703 that may be used to enter data, and a monitor 704 that is connected to and displays data from the computer 701. The computer of one embodiment has within it a modem attached a phone cord 705, which provides connectivity to a telephone network.

In operation, the computer 701 receives test data from the optical scanner 702. If the hardware within the optical scanner 702 is capable of analyzing the scanned image of the test device it may report result data to the computer, or it may simply provide an electronic image of the test device to the computer. If electronic image data is reported to the computer, the computer may execute software to analyze the image and produce test result data.

In alternate embodiments, the computer may report either the results of the test as read from the test device, or an electronic image of the test device, or both. These results and other data are displayed on monitor 704, which is connected to and controlled by the computer 701. Instructions or data may be entered via the keyboard 703 to direct operation of the computer 701, the optical scanner 702, or to provide additional data related to the test.

Upon completion of reading the test device and entry of all required data, the computer sends the data to the central data location via electronic communications such as telephone network connection 705. Again, data such as the results of the test may be entered both on the form and reported by the reader by electronic network to the central data location where the data is compared to verify that data reported for the same test subject from multiple sources is consistent, thereby ensuring reporting accuracy. In alternate embodiments, other electronic connections such as an Ethernet connection to the Internet may be used in place of telephone network connection 705.

The invention describe herein includes a method of performing drug test to determine whether a bodily fluid sample contains specific substances of abuse. An on-site screening test provides a preliminary test result either by visual or machine analysis of a screening test device, and the result and user data are entered on a special provided form. An electronic image of the form is sent to a central data location, where it is received and the data on the form is recognized by machine and stored. If the on-site screening test provided a nonnegative result a sample is sent to a laboratory for further testing, and if the test provides only negative results no further testing is done. The testing laboratory performs further testing for verification of nonnegative screening test results, and all data is collected at the central data location. Results are then reported to the client or whoever the client designates to receive test results.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the invention. It is intended that this invention be limited only by the claims, and the fall scope of equivalents thereof.

We claim:

1. A method of testing an analyte collected at a test site remote from a testing laboratory to determine whether the analyte contains one or more selected substances, comprising:

testing a portion of an analyte sample with at least one on-site screening test;

entering data onto a provided form comprising form identification and written data including on-site screening results and analyte sample identification;

sending electronically an image of the form from the remote test site to a central data location;

receiving electronically the image of the form at the central data location and automatically recognizing and storing the data contained thereon;

sending one or more of at least one sealed containers containing the analyte to the testing laboratory if the on-site screening test provided a non-negative result;

testing analyte from the sent container at the testing laboratory to determine whether the analyte contains one or more selected substances;

storing results of the test with the stored data; and reporting the stored data.

2. The method of claim 1, further comprising distributing the analyte between at least two containers.

3. The method of claim 1, further comprising sealing each of the at least one sealed containers with a seal comprising identification data and that is verified with a signature.

4. The method of claim 3, further comprising receiving one or more of the sent containers at the testing laboratory and identifying the at least one sealed containers by matching the seal identification data to the scanned and stored data.

5. The method of claim 1, further comprising manually verifying the stored data by comparing it to the received electronic image.

6. The method of claim 1, wherein the analyte is urine.

7. The method of claim 6, wherein the one or more selected substances are one or more selected drugs of abuse.

8. A method of testing an analyte to determine whether the analyte contains one or more selected substances, comprising:

collecting the analyte;

distributing the analyte between at least one container and at least one on-site screening test;

sealing one or more of the at least one containers with a seal comprising identification data and verified by the test subject;

testing the collected analyte with said at least one on-site screening test; and sending electronically an image of a provided form comprising form identification data and data including on-site screening test results, test subject identification data, and chain-of-custody information.

9. The method of claim 8, further comprising destroying one or more of the at least one sealed containers if the on-site screening test indicates the analyte does not contain the one or more selected substances.

10. The method of claim 8, wherein the analyte is urine.

11. The method of claim 10, wherein the one or more selected substances are one or more selected drugs of abuse.

12. A method of testing an analyte to determine whether the analyte contains one or more selected substances, comprising:

receiving electronically an image of a provided form comprising data including on-site screening test results, test subject identification data, and chain-of-custody information;

recognizing and storing automatically the data contained in the image of the provided form;

receiving one or more sealed containers containing collected analyte and sent from an on-site screening location;

testing the analyte from the one or more sealed containers to determine whether the analyte contains the one or more selected substances.

13. The method of claim 12, further comprising identifying the one or more sealed containers by matching a seal including identification data and verified with a signature on the one or more sealed containers to the scanned and stored data.

14. The method of claim 12, further comprising manually verifying the stored data by comparing it to the received electronic image.

15. A machine-readable medium with instructions stored thereon for execution on a computer, the instructions operable to cause the computer to:

receive electronically an image of a provided form comprising data including on-site screening test results, test subject identification data, and chain-of-custody information; and recognize and store automatically the data contained in the image of the provided form.

16. The machine readable media of claim 15, further operable to cause the computer to:

store the results of a laboratory test with the stored data; and report the stored data to a client.

17. A test device reader, comprising:

a test device receiver capable of receiving and holding a test device;

an optical scanner operable to scan an image of a test device held in the test device receiver; and an electronic circuit operable to analyze the image of the test device and report a test result.

18. The test device reader of claim 17, further comprising an electronic data communications circuit capable of electronically sending a test result to a remote location.

19. The test device reader of claim 17, further comprising a keyboard for controlling the reader and for entering data associated with the test result.

20. A method of testing, comprising:

testing a portion of an analyte with at least one screening test;

entering data onto a form comprising data including a screening test result;

sending electronically an image of the form to a central data location;

receiving electronically the image of the form at the central data location and automatically recognizing and storing the data contained thereon;

sending a container containing a portion of the analyte to the testing laboratory if the screening test provided a non-negative result;

testing analyte from the container at the testing laboratory to determine whether the analyte contains one or more selected substances;

storing results of the test with the stored data; and reporting the stored data.

21. A method of testing a urine sample collected at a test site remote from a testing laboratory to determine whether a test subject has used one or more selected substances, comprising:

testing urine from the urine sample with at least one on-site screening test;

entering data onto a provided form comprising form identification and data including on-site screening results, test subject identification, and chain-of-custody information;

sending electronically an image of the form from the remote test site to a central data location;

receiving electronically the image of the form at the central data location and automatically recognizing and storing the data contained thereon;

sending one or more of at least one containers containing the urine sample to the testing laboratory if the on-site screening test provided a non-negative result;

testing urine from the at least one container at the testing laboratory to determine whether the test subject has used one or more selected substances;

storing results of the test with the stored data; and reporting the stored data to a client.

* * * * *